United States Patent
Zal et al.

(10) Patent No.: US 12,016,956 B2
(45) Date of Patent: Jun. 25, 2024

(54) ANNELID HAEMOGLOBIN LYOPHILISATION PROCESS

(71) Applicant: Hemarina, Morlaix (FR)

(72) Inventors: Franck Zal, Ploujean-Morlaix (FR); Morgane Rousselot, Saint Pol de Leon (FR)

(73) Assignee: Hemarina, Morlaix (FR)

( * ) Notice: Subject to any disclaimer, the term of this patent is extended or adjusted under 35 U.S.C. 154(b) by 471 days.

(21) Appl. No.: 17/014,445

(22) Filed: Sep. 8, 2020

(65) Prior Publication Data

US 2021/0113471 A1  Apr. 22, 2021

Related U.S. Application Data

(63) Continuation of application No. 14/412,786, filed as application No. PCT/FR2013/051271 on Jun. 5, 2013, now abandoned.

(30) Foreign Application Priority Data

Jun. 5, 2012 (FR) ...................... 1255204

(51) Int. Cl.
| | | |
|---|---|---|
| A61K 9/19 | (2006.01) | |
| A61K 35/62 | (2006.01) | |
| A61K 38/17 | (2006.01) | |
| A61K 38/42 | (2006.01) | |
| A61K 47/22 | (2006.01) | |
| A61K 47/26 | (2006.01) | |

(52) U.S. Cl.
CPC ................ *A61K 9/19* (2013.01); *A61K 35/62* (2013.01); *A61K 38/1709* (2013.01); *A61K 38/1767* (2013.01); *A61K 38/42* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | |
|---|---|---|
| 2003/0068416 A1 | 4/2003 | Burgess et al. |
| 2008/0305178 A1 | 12/2008 | Zal et al. |

FOREIGN PATENT DOCUMENTS

| | | |
|---|---|---|
| CN | 101642565 A | 2/2010 |
| WO | 2007/035583 A1 | 4/2003 |
| WO | 2009/007532 A2 | 1/2009 |
| WO | 2009/050343 A2 | 4/2009 |
| WO | 2010/128159 A1 | 11/2010 |
| WO | 2013/001196 A1 | 1/2013 |

OTHER PUBLICATIONS

International Search Report for International Application No. PCT/FR2013/051271 dated Sep. 5, 2013.
Written Opinion for International Application No. PCT/FR2013/051271 dated Sep. 5, 2013.
J.R. Harris et al., "Transmission electron microscopical polychaete Nereis virens," Micron, 32:599-613 (2001).
Johnston et al., "The Influence of Sugars on the Properties on Freeze-Dried Lysozyme and Haemoglobin," Thermochimica Acta, 144:195-208 (1989).
P Labrude et al., "Influence de l'addition d'albumine sur la conservation de la solution d'hemoglobine lyophilisee en presence de glucose," Revue Francaise De Transfusion Et Immuno-Hematologie, 23(1):23-34 (1980).
International Preliminary Report on Patentability for International Application No. PCT/FR2013/051271 dated Sep. 12, 2014.
Bucci, E., et al. 2007 Artif Cells Blood Substit Immobil Biotechnol 35(1): 11-18, NIH Public Access copy: 9 pages total.
Hagen, S.J., et al. 1995 TCB 6: 423-426.

*Primary Examiner* — Marsha Tsay
(74) *Attorney, Agent, or Firm* — McAndrews, Held & Malloy, Ltd.

(57) ABSTRACT

The present invention relates to a lyophilizate comprising at least one globin, one globin protomer or one extracellular hemoglobin of annelids, and a stabilizer chosen from disaccharides, polyols and antioxidants. The present invention also relates to a composition comprising: a solution comprising at least one globin, one globin protomer or one extracellular hemoglobin of annelids, and a stabilizer chosen from disaccharides, polyols and antioxidants.
Finally, the present invention relates to a process for preparing the lyophilizate.

9 Claims, 1 Drawing Sheet

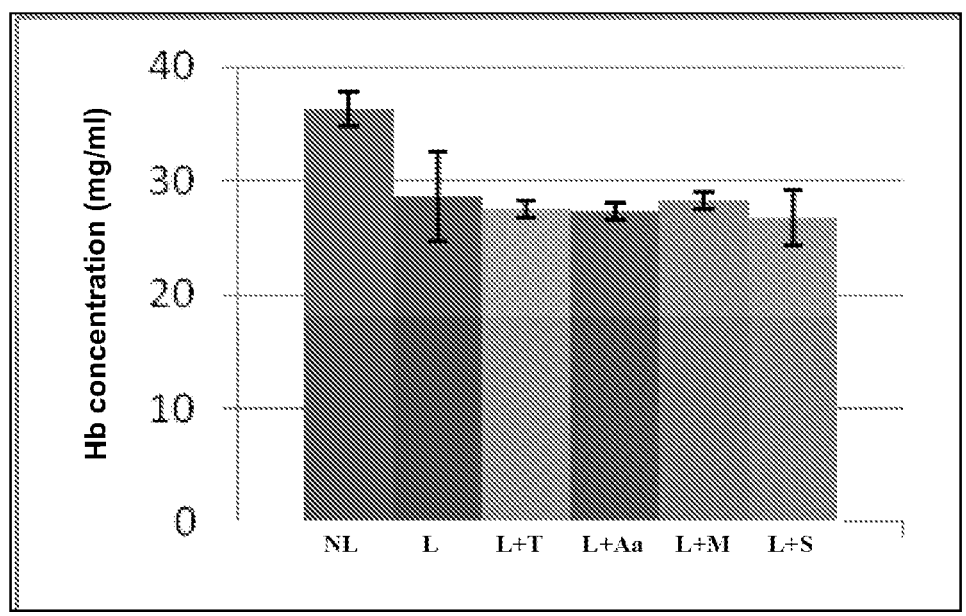

ANNELID HAEMOGLOBIN LYOPHILISATION PROCESS

The present application claims priority to, and is a continuation application of, U.S. patent application Ser. No. 14/412,786, filed Jan. 5, 2015, which is a U.S. National Phase application of International Patent Application No. PCT/FR2013/051271, filed Jun. 5, 2013, claiming the benefit of priority to French Patent Application No. 1255204, which was filed on Jun. 5, 2012. The entire text of the aforementioned applications is incorporated herein by reference in its entirety.

The present invention relates to a process for the lyophilization of at least one extracellular hemoglobin, globin protomer or globin of annelids, and also to the lyophilisate obtained.

BRIEF DESCRIPTION OF THE DRAWINGS

Aspects of the present disclosure will now be described, by way of example only, with reference to the attached Figures, wherein:

FIG. 1. Details monitoring of the hemoglobin concentration after reconstitution.

DETAILED DESCRIPTION

The extracellular hemoglobin of annelids is of use as a blood substitute, and makes it possible to treat problems associated with an oxygen deficiency.

The term "blood substitute" is intended to mean any product or solution which makes it possible to compensate for a blood loss following a hemorrhage by providing oxygen carriers. A blood substitute is different than an artificial blood, since the blood substitute cannot perform all the functions provided by blood, such as hormone transport for example.

Currently, two pharmaceutical classes of substitution products are already known: they are perfluorocarbons (PFCs) and hemoglobin oxygen carriers (HBOC).

PFCs are chemically synthesized compounds which allow the transport of $O_2$ in dissolved form in the bloodstream and to the tissues.

HBOCs come from the purification and then chemical modification of bovine HB or human HB (the latter coming from expired blood bags) or are alternatively derived from synthesis by genetic engineering.

In order to store HBOCs, a conventional method consists in conditioning the hemoglobin molecules in solution. In order to guarantee better stability, in some cases, it is necessary to store them between −20° C. and −80° C. before their use. They are then transported in dry ice in order to ensure that there is no thawing. These various conditions involve an additional cost and more restrictive storage and transportation logistics which can prove to be limiting for certain applications.

There is therefore a need to have a functional hemoglobin which is easily stored and transported, including in remote environments without refrigeration.

Solutions exist, and one of them is lyophilization.

However, preliminary studies have revealed that the hemoglobin molecules are partly degraded by the lyophilization process, thereby in particular impairing their functionality, namely their ability to reversibly bind oxygen. This is, moreover, described in the literature for proteins in general (Heller Martin. C, Carpenter John. F, Randolph Theodore. W, "Protein Formulation and Lyophilization Cycle Design: Prevention of Damage due to Freeze-Concentration Induced Phase Separation" Biotechnology and Bioengineering, Vol 63, No. 2, 1999).

The inventors have discovered that, surprisingly, the extracellular hemoglobin of annelids, when it is mixed with a specific stabilizer, can be lyophilized, while at the same time preserving its quaternary structure, its functionality and its efficacy.

The present invention thus relates to a process for the lyophilization of at least one extracellular hemoglobin, globin protomer or globin of annelids. The present invention also relates to the lyophilisate thus obtained. The latter in fact makes it possible to store the extracellular hemoglobin of annelids, its globin(s) and its globin protomer(s) in a format which is economical and practical (i.e. it requires a minimum amount of space), while at the same time preserving the structural and functional properties of the hemoglobin.

The lyophilizate according to the invention comprises at least one extracellular hemoglobin, globin protomer or globin of annelids, and a stabilizer chosen from disaccharides, polyols and antioxidants.

The present invention also relates to a composition comprising:
- a solution comprising at least one extracellular hemoglobin, globin protomer or globin of annelids, and
- a stabilizer chosen from disaccharides, polyols and antioxidants, preferably chosen from trehalose and ascorbic acid.

The extracellular hemoglobin of annelids is present in the three classes of annelids: the polychaetes, the oligochaetes and the achaetes. Reference is made to extracellular hemoglobin because it is not naturally contained in a cell, and can therefore circulate freely in the bloodstream without chemical modification to stabilize it or make it functional.

The extracellular hemoglobin of annelids is a giant biopolymer with a molecular weight of between 2000 and 4000 kDa, consisting of approximately 200 polypeptide chains comprising between 4 and 12 different types which are generally grouped into two categories.

The first category, with 144 to 192 components, groups together the "functional" polypeptide chains which bear an active site of heme type, and are capable of reversibly binding oxygen; these are chains of globin type, the weights of which are between 15 and 18 kDa and which are very similar to the α- and β-type chains of vertebrates.

The second category, with 36 to 42 components, groups together the "structural" or "linker" polypeptide chains which have few or no active site but enable the assembly of the subunits called one-twelfth subunits or protomers.

Each hemoglobin molecule consists of two superposed hexagons which have been named hexagonal bilayer and each hexagon is itself formed by the assembly of six subunits (or "one-twelfth subunits" or "protomers") in the form of a drop of water. The native molecule is made up of twelve of these subunits (dodecamer or protomer). Each subunit has a molecular weight of between 200 and 250 kDa, and constitutes the functional unit of the native molecule.

Preferably, the extracellular hemoglobin of annelids is chosen from the extracellular hemoglobins of polychaete annelids, preferably from the extracellular hemoglobins of the family Arenicolidae and the extracellular hemoglobins of the family Nereididae. Even more preferentially, the extracellular hemoglobin of annelids is chosen from the extracellular hemoglobin of *Arenicola marina* and the extracellular hemoglobin of *Nereis*, more preferentially the extracellular hemoglobin of *Arenicola marina*.

According to the invention, the lyophilizate or the composition may also comprise at least one globin protomer of the extracellular hemoglobin of annelids. Said protomer constitutes the functional unit of native hemoglobin, as indicated above.

Finally, the lyophilizate or the composition may also comprise at least one globin chain of the extracellular hemoglobin of annelids. Such a globin chain may in particular be chosen from the Ax and/or Bx type globin chains of extracellular hemoglobin of annelids.

The extracellular hemoglobin of annelids and globin protomers thereof have an intrinsic superoxide dismutase (SOD) activity, and the presence of antioxidant is not required in order for them to function, contrary to the use of a mammalian hemoglobin, for which the antioxidant molecules are contained inside the red blood cell and are not bonded to the hemoglobin. Furthermore, the extracellular hemoglobin of annelids, globin protomers thereof and/or globins thereof do not require a cofactor in order to function, contrary to mammalian hemoglobin, in particular human hemoglobin. Finally, the extracellular hemoglobin of annelids, globin protomers thereof and/or globins thereof do not possess blood typing; they make it possible to avoid any problem of immunological reaction.

The extracellular hemoglobin of annelids, globin protomers thereof and/or globins thereof may be native or recombinant.

The composition according to the invention also comprises a solution. This solution is capable of creating a saline environment suitable for the hemoglobin, protomers thereof and globins thereof, and thus makes it possible to maintain the quaternary structure, and therefore the functionality of this molecule. By virtue of the solution, the hemoglobin, protomers thereof and globins thereof are capable of performing their oxygenation function.

The solution according to the invention is an aqueous solution comprising salts, preferably chloride, sodium, calcium, magnesium and potassium ions, and confer on the composition according to the invention a pH of between 6.5 and 7.8; its formulation is similar to that of a physiologically injectable liquid. Under these conditions, the extracellular hemoglobin of annelids, globin protomers thereof and globins thereof remain functional.

In the present description, the pH is understood to mean at ambient temperature (20±5° C.), unless otherwise mentioned.

Preferably, the solution is an aqueous solution comprising sodium chloride, calcium chloride, magnesium chloride, potassium chloride, and also sodium gluconate and sodium acetate, and has a pH of between 6.5 and 7.8, preferably equal to 7.1±0.5, preferably of approximately 7.35. More preferentially, the stabilizing solution is an aqueous solution comprising 0-100 mM of NaCl, preferably 90 mM of NaCl, 23 mM of Na gluconate, 2.5 mM of $CaCl_2$, 27 mM of Na acetate, 1.5 mM of $MgCl_2$, 5 mM of KCl, and has a pH of 7.1±0.5, possibly containing between 0 and 100 mM of antioxidant of ascorbic acid and/or reduced glutathione type. Said solution preferably has an osmolarity of between 300 and 450, preferably between 300 and 350, and preferentially of 302 mOsmol/l.

The composition and the lyophilizate according to the invention also comprise a stabilizer. This stabilizer maintains the quaternary structure and therefore the functionality of the hemoglobin, globins thereof and protomers thereof, even after lyophilization.

The term "stabilizer" is intended to mean a disaccharide, a polyol and/or an antioxidant. The disaccharides comprise in particular sucrose, trehalose and raffinose, preferably trehalose. The effectiveness of the stabilizer is determined by comparing the physicochemistry and the functional properties of the hemoglobin before and after lyophilization.

The stabilizer according to the invention is chosen from disaccharides, polyols and antioxidants.

Preferably, the disaccharides are chosen from trehalose and sucrose. More preferentially, the disaccharide is trehalose. Preferably, the polyols are chosen from mannitol and sorbitol. Finally, preferably, the antioxidant is ascorbic acid.

Trehalose is also called α-D-glucopyranosyl-α-D-glucopyranoside or alpha,alpha-trehalose, or α-D-glucopyranosyl-α-D-glucopyranoside dihydrate. It is a disaccharide composed of two glucose molecules linked together by a particularly stable α,α-1,1 (or "1,1-α-glycosidic") bond.

Sucrose is a disaccharide formed by the condensation of a glucose molecule with a fructose molecule. Its chemical name is β-D-fructofuranosyl-(2↔1)-α-D-glucopyranoside.

Mannitol, or 1,2,3,4,5,6-hexanehexol, and sorbitol, or (2R,3S,4S,5S)-hexane-1,2,3,4,5,6-hexol, are polyols.

Finally, ascorbic acid is an organic acid which has antioxidant properties. It may be present in D or L form. Preferably, the stabilizer is L-ascorbic acid, or vitamin C Preferably, the stabilizer is chosen from trehalose and ascorbic acid. Preferably, the composition and/or the lyophilizate according to the invention comprise trehalose and ascorbic acid.

The composition and the lyophilizate according to the invention may comprise salts. These salts can be chosen from sodium, calcium, magnesium and potassium salts. Preferably, the salts are chosen from sodium chloride, calcium chloride, magnesium chloride, potassium chloride, sodium gluconate and sodium acetate.

A subject of the invention is also a process for preparing a lyophilizate, comprising:
i) the mixing of a solution comprising at least one extracellular hemoglobin, globin protomer or globin of annelids with a stabilizer chosen from disaccharides, polyols and antioxidants,
ii) the freezing of the mixture obtained in i) at a temperature of between −10° C. and −100° C., preferably between −20° C. and −100° C., for a time of at least 24 h, preferably at least 48 h;
iii) the sublimation of the frozen mixture obtained in ii) for at least 2 h, under vacuum;
iv) the final drying of the mixture obtained in iii), until a powder is obtained.

The mixing of step i) is carried out in particular by vortexing.

Preferably, the stabilizer, in particular the disaccharide or the polyol, is present in the mixture of step i) of the process according to the invention in a concentration of between 1 and 500 mg/ml. Alternatively, the stabilizer, in particular the antioxidant, is present in the mixture of step i) in a concentration of between 3 and 20 mM. Even more preferentially, the stabilizer present in the mixture of step i) is chosen from:
trehalose and sucrose which are present in a concentration of between 50 and 70 mg/ml, preferably of approximately 55 mg/ml or 65 mg/ml,
trehalose and sucrose which are present in a concentration of approximately 100 mg/ml,
mannitol which is present in a concentration of between 50 and 100 g/l, and
ascorbic acid which is present in a concentration of approximately 5 mM.

The solution obtained at the end of step i) thus comprises at least one extracellular hemoglobin, globin protomer or globin of annelids, and the stabilizer.

This solution is subjected to lyophilization. The lyophilization cycle may comprise three steps:

freezing (step ii) of the process according to the invention):

This first phase consists in freezing the solution in such a way that the water contained is converted into ice.

Preferably, the freezing of step ii) of the process according to the invention is carried out at a temperature of between −10° C. and −100° C., preferably between −20° C. and −90° C., for at least 24 h, preferably at least 48 h. Preferably, the freezing is carried out at approximately −20° C. for at least 24 h, preferably at least 48 h;

primary desiccation or sublimation (step iii) of the process according to the invention):

The sublimation step allows the ice present in the frozen solution to go from the solid state to the gas state, without an intermediate step. The frozen solution is dried out by the application of a vacuum; the ice then becomes vapor.

The sublimation is carried out using a high-vacuum pump, a mechanical pump or a cryopump.

Preferably, the sublimation of step iii) is carried out for at least 4 h;

secondary desiccation or final drying (step iv) of the process according to the invention):

When the ice is totally sublimated, the secondary desiccation phase can begin. It makes it possible to extract, by desorption, the water molecules trapped at the surface of the dried products.

At the end of the lyophilization, and therefore of the process according to the invention, the lyophilizate obtained comprises between 0.1% and 5% by weight of water.

The lyophilizate is a powder, which completely redissolves in a hydrophilic liquid, without insoluble residues. The powder can be stored in glass or plastic, preferably glass, bottles or flasks.

The lyophilized hemoglobin thus obtained is easy to transport and to store. The lyophilizate according to the present invention is thus easy to reconstitute and is ready to be used.

The present invention also relates to a composition comprising the lyophilizate according to the invention, and a diluent. The lyophilizate can in fact be diluted at the appropriate moment with a diluent, in order to restore the initial hemoglobin solution. Preferably, the diluent is ultrapure water, so as not to modify the concentration of the salts of the solution, and to obtain a composition having a volume equivalent to that of before the lyophilization.

The invention is described in greater detail in the following examples. These examples are given solely for the purposes of illustration, and are not limiting.

EXAMPLE 1

Materials and Methods
Study Protocol

The inventors evaluated the effects of the lyophilization and the impact of the excipients added to the formation on:
the quaternary structure of the hemoglobins,
the functionality: ability to bind oxygen,
the effectiveness of the hemoglobins in cell models.

Hemoglobin (Hb) Preparation

The same batch of Hb was used for all the studies. A calculated amount of Hb is thawed at 5±3° C. for 1 hour. Once thawed, the required amount of excipient is added in liquid form so as to achieve the desired concentration.

The solution thus obtained is frozen at −80° C. for at least 24 h. The frozen solution is then lyophilized in the lyophilizer for approximately 4 h until a powder is obtained. This powder is then stored at −80° C. before the stability study.

The reconstitution is carried out with ultrapure water so as not to modify the salt concentration and in a volume equivalent to that of before lyophilization.

Analytical Tools

The product monitoring study comprises three phases: monitoring of the structure of the molecule, monitoring of its functionality and, finally, monitoring of the hemoglobin concentration.

Monitoring the Structure

The structure is monitored by means of a protein-specific chromatography method: FPLC (Fast Protein Liquid Chromatography). It uses the principle of size exclusion. The system used is sold by Dionex® under the trade name Ultimate 3000. It is entirely automated and controlled by the accompanying Chromeleon® software.

The columns used are sold by GE Healthcare® and are of the Superose 6, 10×300 mm type; they make it possible to separate molecules of which the molecular weight is between 5 MDa and 5000 Da in one hour at a flow rate of 0.5 ml/min. The separation is carried out under isocratic conditions, i.e. there is just one elution buffer.

The acquisition in the context of the hemoglobin studies is carried out at 2 wavelengths (280 nm and 414 nm). In order to detect the target molecule, hemoglobin, the optical density is measured at 280 nm (protein absorption peak) and at 414 nm (heme absorption peak). The acquisition at 414 nm makes it possible to identify the hemoglobin among the other proteins observed at 280 nm. At this same wavelength, it is also possible to monitor the hemoglobin dissociation kinetics. The Chromeleon® software provided with the equipment makes it possible both to harvest the data and also to process them.

The data processing is carried out by analysis of the chromatograms obtained at 280 nm and at 414 nm.

The software makes it possible to integrate the chromatograms:
the area under the curve of the peak of interest is proportional to the concentration;
the relative percentage purity of each peak calculated by the software makes it possible to monitor the evolution of the degradation of the molecule over time.

In the case of the study, kinetics making it possible to quantify the effects of the excipients selected and the behavior of the molecule over the course of one week are performed. For this, the chromatograms of each excipient are integrated at each point (from time $T_0$ up to day 5) and then the data generated by the software (the area under the curve and the relative percentage purity) are processed graphically using the Graphpad® software in order to determine the degradation kinetics and to compare them.

Monitoring of the Functionality

The functionality of the hemoglobin molecule is defined by its ability to reversibly bind oxygen. This study is possible with UV-visible spectrophotometry.

Hemoglobin has a characteristic spectrophotometric signature which changes according to its functionality and its oxidation state. The measurement is carried out on a window of wavelengths of between 250 and 700 nm. Thus, absorption spectra which are different according to the oxidation state are obtained.

For example, the hemoglobin of *Arenicola marina* (HbAm) exhibits, in its oxygenated state, two peaks in the visible range, i.e. the alpha and beta bands respectively present at 576 nm and 540 nm, and a "Soret" band at 414 nm. The first mentioned are characteristic of the absorption of the complex formed between the heme group, iron and oxygen. The Soret band is, for its part, synonymous with the absorption of the complex formed between the polypeptide chain and the heme group.

Hemoglobin has spectral properties characteristic of its changes in conformation between the oxygenated and non-oxygenated states.

Thus, depending on the maxima noted, the various states of the hemoglobin can be determined by referring to the following table:

| Soret band | Alpha band | Beta band | Hemoglobin form |
| --- | --- | --- | --- |
| 414 ± 2 nm | 540 ± 2 nm | 576 ± 2 nm | Oxyhemoglobin |
| 430 ± 2 nm | 555 ± 2 nm | 555 ± 2 nm | Deoxyhemoglobin |
| 418 ± 2 nm | 535 ± 2 nm | 570 ± 2 nm | Carboxyhemoglobin |
| 406 ± 2 nm | 500 ± 2 nm | 630 ± 2 nm | Methemoglobin |

Finally, the percentage of oxidized hemoglobin can be determined. The UV-visible spectra acquired between 250 and 700 nm are standardized at 523 nm (isobestic point). The absorbances at 576 nm (alpha band) and 540 nm (beta band) are added for each spectrum. Likewise, the absorbances for a reference sample ideally not exhibiting oxidation (in the case of lyophilization=the D0 of a non-lyophilized sample is chosen as reference) are noted. The same operation is then carried out for a sample considered to be 100% oxidized (obtained by incubation at 37° C. until disappearance of the alpha and beta bands).

The percentage oxidation of the molecule is obtained by means of the following calculation:

$$\% \ Hb \ \text{oxidized} = 100 - \frac{[A \ Hb - A100] \times 100}{A0 - A100}$$

With $A = A_{540} + A_{576}$; $A \ Hb = A_{540} + A_{576}$ of the hemoglobin sample; $A0 = A_{540} + A_{576}$ of the 0% oxidized; $A \ 100 = A_{540} + A_{576}$ of the 100% oxidized.

As for the monitoring of the structure, the spectra are superposed for each condition in order to visualize the effect of the excipients over the course of one week, and then the evolution of the oxidation percentages is processed graphically using the Graphpad® software in order to determine the auto-oxidation kinetics under the various conditions tested.

Monitoring the Concentration

The hemoglobin is assayed by spectrophotometry using Drabkin's reagent which makes it possible to accurately assay the heme, which is the active side of the hemoglobin.

Effectiveness Tests

In order to evaluate the effectiveness of the hemoglobins of *Arenicola marina* (HbAm) and of *Nereis* (HbN), two cell models were developed in the laboratory, each representative of the applications to which the molecules are dedicated.

For HbAm, this involves a cell model which mimics the storage conditions for organs awaiting transplantation. A cell toxicity test is used in order to evaluate the lesions caused by the cold storage: this test corresponds to the release of lactate dehydrogenase (LDH). LDH is an enzyme present in the cytosol of cells and its release into the culture supernatant reflects plasma membrane permeabilization and therefore cell death. The effectiveness of the HbAms is evaluated by comparing the percentage LDH release under the organ storage conditions with and without HbAm.

The second model developed is based on the application of the HbN molecule in the context of the bioproduction of recombinant proteins. The cell line corresponds to a line commonly used for bioproduction. The cells are seeded at a predetermined cell density in the presence or absence of a known amount of HbN. After 4 days of culture, the cell density and the cell viability are measured. The effectiveness of the HbNs is evaluated by comparing the cell growth and viability under the culture conditions with and without HbN.

Results for HbAm

Monitoring of the stability of HbAm after reconstitution ($T_0$)

Monitoring of the Hemoglobin Concentration after Reconstitution

The results of the HbAm assay after reconstitution following the lyophilization step indicate a decrease in the Hb concentration after reconstitution, whatever the lyophilization conditions (see FIG. 1: legend: NL=Non-lyophilized; L=Lyophilized; L+T=Lyophilized with trehalose; L+Aa=Lyophilized with ascorbic acid; L+M=Lyophilized with mannitol; L+S=Lyophilized with sucrose). This loss of less than 10% indicates that the lyophilization decreases the hydrophilic capacity of the molecule.

Monitoring of the Structural Stability at T0

The HbAm purity percentages at 280 nm and at 414 nm are similar for the various compositions tested.

In the light of the standard deviations, the results obtained show that there is no significant difference in purity between the various conditions tested. Thus, at T0, after reconstitution, the quaternary structure of the HbAm is not significantly affected, either by the lyophilization or by the presence of the various excipients.

Monitoring of the Functionality of Reconstituted HbAm

In order to judge as accurately as possible the impact of the lyophilization on the functionality of the molecule after reconstitution ($T_0$), the percentage oxidation and the modifications of the spectrophotometric signature of the hemoglobin are measured.

The lyophilization process causes an oxidation of the molecule of approximately 20% compared with the non-lyophilized molecule. All the excipients tested, and in particular the ascorbic acid and the trehalose, show a positive effect on the protection of the molecule against oxidation.

The trehalose and the ascorbic acid made it possible both to protect the molecule against the oxidation induced by the lyophilization process and also to reduce the proportion of molecule initially oxidized.

The study of the UV-visible spectra shows that the various conditions tested do not significantly affect the functionality of HbAm after reconstitution: the Soret, alpha and beta bands are present at the wavelengths of a functional hemoglobin (cf. table 1). In the case of the hemoglobin lyophilized alone, although 20% oxidation is observed, the molecule remains functional overall.

TABLE 1

Wavelengths noted on the UV-visible spectra of the various conditions

| Conditions | Soret band | Alpha band | Beta band | Functionality |
| --- | --- | --- | --- | --- |
| HbAm NL | 414 nm | 540 nm | 574 nm | Oxyhemoglobin |
| HbAm L | 412 nm | 538 nm | 574 nm | |
| HbAm L + Trehalose | 414 nm | 538 nm | 574 nm | |

TABLE 1-continued

Wavelengths noted on the UV-visible spectra of the various conditions

| Conditions | Soret band | Alpha band | Beta band | Functionality |
|---|---|---|---|---|
| HbAm L + Mannitol | 412 nm | 538 nm | 574 nm | |
| HbAm L + Sucrose | 414 nm | 538 nm | 574 nm | |
| HbAm L + Ascorbic acid | 414 nm | 540 nm | 574 nm | |

NL = Non-lyophilized
L = Lyophilized

Conclusions

This preliminary step shows that the lyophilization of HbAm does not significantly modify the quaternary structure of the molecule. However, the lyophilization causes a partial oxidation of the hemoglobin. The results show that the excipients tested make it possible to protect the molecule from the oxidation induced by the lyophilization process without affecting its quaternary structure. Moreover, among the excipients tested, trehalose and ascorbic acid give the best protection against oxidation.

Monitoring of the Stability of HbAm Over the Course of 5 Days

This study is carried out on the samples reconstituted after lyophilization with and without excipients and compared to the non-lyophilized molecule.

Said samples are reconstituted at $T_0$ with ultrapure water and then incubated at 37° C. so as to accelerate the degradation of the molecule in order to evaluate the effects of the chosen excipients. The structural and functionality analyses and also the assaying of the hemoglobin are carried out each day ($D_0$, $D_1$, $D_2$, $D_3$, $D_4$).

Monitoring of the Hemoglobin Concentration

The results show a relative decrease in the amount of hemoglobin. This decrease, characteristic of a degradation or adsorption of the hemoglobin, is observed for the non-lyophilized molecule, and also the molecule lyophilized in the presence of ascorbic acid, mannitol and sucrose. No significant decrease for the molecule lyophilized alone and in the presence of trehalose is observed.

Monitoring of the Quaternary Structure

The percentage purity is measured at 280 nm over time. The processing of the data (Graphpad® software) makes it possible to determine a trend curve characteristic of the molecule degradation kinetics. Two trends stand out:
 a linear regression for all the conditions except trehalose;
 a plateau followed by a decrease phase for trehalose.

The results show that ascorbic acid appears to maintain the structural integrity of the HbAm molecule. Specifically:
 the least stable molecule is the molecule lyophilized alone: $T_{1/2}=2.9$ days and $k_d=0.17$ $d^{-1}$; and
 the molecule lyophilized in the presence of trehalose or of ascorbic acid is the most stable with $T_{1/2}=5.4$ and 4.7 days respectively, and $k_d=0.12$ and $0.10$ $d^{-1}$ respectively.

Monitoring of the Functionality

As for the monitoring of the structure, the oxidation data were analyzed with Graphpad® in order to determine the molecule oxidation kinetics.

The evolution of the percentage oxidation over time can be represented by a sigmoid curve of the dose-response type for 3 conditions: lyophilized alone; lyophilized with trehalose and sucrose.

The dose-response aspect can be explained by double kinetics: the first corresponding to the auto-oxidation of the molecule: the conversion of the ferrous iron to ferric iron and the formation of radical $O_2$ ($O_2 \cdot^-$). Radical $O_2$ is an oxidizing species which catalyses the oxidation reaction (equation below).

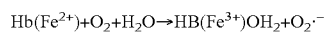

$$Hb(Fe^{2+})+O_2+H_2O \rightarrow HB(Fe^{3+})OH_2+O_2\cdot^-$$

Ascorbic acid and trehalose "capture" $O_2\cdot^-$, preventing its interaction with Hb: this explains the linear profile of the oxidation kinetics in the presence of these excipients. The study of the UV-visible spectra (results not shown) shows that the functionality of the hemoglobin is maintained up to $D_3$ for the samples composed of ascorbic acid and up to $D_2$ for those containing trehalose.

Conclusions

During this short-term study, the predominance of two excipients was observed for maintaining the structure and the functionality and for slowing down the oxidation of the molecule once reconstituted; these are trehalose and ascorbic acid.

Evaluation of the Effectiveness of HbAm

The results show that, for all the conditions tested, compared to the control, i.e. to the preserving medium alone, the LDH release percentages are lower than those of said medium.

This shows that HbAm is effective whatever the conditions. However, it is more or less effective depending on the excipients used during the lyophilization.

A significant difference is noted between the non-lyophilized molecule and the molecule lyophilized in the presence of ascorbic acid, which is the most effective. Finally, the lyophilized molecule appears to be more effective than the non-lyophilized molecule and than the molecule lyophilized+trehalose.

Study of the Stability of HbAm in the Lyophilized State

The results presented here are very preliminary

Monitoring of the Hemoglobin Concentration

The evolution of the concentration over time under the various conditions studied shows that there are no significant differences up to $D_2$. From $D_2$ onward, the redispersion appears to be more difficult.

Monitoring of the Structural Stability

The results obtained for the monitoring of the quaternary structure of the molecule show surprising profiles in the case of the molecule treated with ascorbic acid.

The plots could not be integrated starting from $D_1$. This is because the peak corresponding to the hemoglobin is destructured.

A comparison between the purity of the molecule lyophilized alone or with trehalose was carried out.

In the case of the lyophilized molecule, the curve describes a linear trend ($R^2=0.9858$). The molecule supplemented with trehalose appears to be more stable. Indeed, the profile of the curve shows a slight decrease between $D_0$ and $D_1$ and then a stability phase up to $D_3$.

Monitoring of the Functional Stability

In the light of the evolution of the percentage oxidation, ascorbic acid and trehalose also appear to be effective. The first describes an increase in linear evolution, while the second exhibits a slight increase and then a stability phase. These experiments will have to be reproduced in order to confirm these first observations.

Results for HbN

All the experiments carried out in the context of the monitoring of HbAm stability are applied to HbN.

Monitoring of the Stability of HbN at $T_0$

Monitoring of the Hemoglobin Concentration at $T_0$

The results of the hemoglobin assay after reconstitution of the HbN molecule under the various conditions do not show any significant difference between the non-lyophilized molecule, the molecule lyophilized+trehalose and the molecule lyophilized+mannitol. However, a loss of hemoglobin after lyophilization of the molecule alone, supplemented with sucrose or supplemented with ascorbic acid is noted.

In the present case both mannitol and trehalose, have a positive effect on reconstitution.

Monitoring of the Structural Stability of HbN after Reconstitution

The percentage purity measured at $T_0$ at 280 nm (A) and 414 nm (B) does not, in the light of the standard deviations, show any significant difference at 280 nm, whatever the state of the molecule (lyophilized or non-lyophilized) and the excipients tested. The same is true for the percentage purity at 414 nm. Thus, the lyophilization does not appear to induce destructuring of the molecule.

Monitoring of the Functionality of the HbN Molecule at T0

The relative percentage oxidation obtained after lyophilization and calculated on the basis of the non-lyophilized molecule is measured.

The monitoring of the oxidation state of the molecule at $T_0$ shows an oxidation of 35% for the molecule lyophilized alone, i.e. 15% higher than the HbAm molecule. All the excipients tested provide the hemoglobin with protection against oxidation. Specifically, the percentage oxidation noted at $T_0$ is between 10% for trehalose and −20% for ascorbic acid which is the most protective. The effect of trehalose is less effective for HbN than for HbAm. The UV-visible spectra of the various samples exhibit perfect superposition with a spectral signature of a functional hemoglobin.

Thus, the functionality of the HbN molecule, like HbAm, is not significantly affected by the lyophilization process.

Conclusions

At the end of this step, all the excipients tested maintain the structure of the molecule and its functionality and also provide the molecule with effective protection against oxidation, particularly with a treatment with sucrose or with ascorbic acid. Unlike in the case of HbAm, trehalose provides less effective protection against oxidation. Indeed, in the case of HbN, the oxidation is reduced (10%), but not obliterated.

The action of all the excipients tested will therefore be evaluated over the course of 5 days in order to select the most effective thereof.

Monitoring of the Stability of Reconstituted HbN Over the Course of 5 Days

Monitoring of the Hemoglobin Concentration

The evolution of the hemoglobin concentration over time shows that, whatever the condition considered, the hemoglobin concentration remains stable.

Monitoring of the Quaternary Structure

The evolution of the percentage purity at 280 nm shows that the various kinetics adopt a linear trend (table 2).

TABLE 2

HbN trend curves and associated constants

| Condition tested | Trend curve | Equation | $R^2$ | Half-life $T_{1/2}$ (d) | Associated constants $k_d$ (d$^{-1}$) |
|---|---|---|---|---|---|
| NL | | | 0.9755 | 0.1643 ± 0.01502 | 3.043 |
| L | Linear regression | $\frac{\% \text{ purity (t)}}{\% \text{ purity (t0)}} = -k \times t$ | 0.9874 | 0.1714 ± 0.01119 | 2.917 |
| L + Trehalose | | | 0.9737 | 0.1820 ± 0.01727 | 2.747 |
| L + Ascorbic acid | | | 0.9952 | 0.04049 ± 0.001995 | 12.348 |
| L + Mannitol | | | 0.9719 | 0.03847 ± 0.004627 | 12.997 |
| L + Sucrose | | | 0.9539 | 0.03423 ± 0.005324 | 14.607 |

(NL = Non-lyophilized HbN; L = Lyophilized HbN)

The data show maintenance of the protein structure provided by sucrose ($T_{1/2}$=14.607; $k_d$=0.03423), mannitol ($T_{1/2}$=12.997; $k_d$=0.03847) and ascorbic acid ($T_{1/2}$=12.348; $k_d$=0.0409). With regard to trehalose ($T_{1/2}$=2.747; $k_d$=0.1820), it lies at the same level as the lyophilized or non-lyophilized samples.

Monitoring of the Functionality

The monitoring of the percentage oxidation of the hemoglobin reveals a protective effect provided by trehalose up to D4 with a percentage oxidation of less than 50%. The other excipients tested show an antioxidant effect at T0 which they gradually lose over the days which follow, until they reach the oxidation level of the non-lyophilized control. The profile of the curves adopts a hyperbolic trend. The oxidation of the molecule is then very quickly catalyzed by radical oxygen. The study of the UV-visible spectra obtained for the conditions tested shows that the functionality is maintained up to D3 when the hemoglobin is treated with trehalose (results not shown here).

Conclusions

At the end of this monitoring over the course of one week, two excipients stand out: trehalose for maintaining the functionality and effective protection against oxidation; ascorbic acid for maintaining the structure of the molecule. Another excipient could be conjugated to trehalose; said other excipient is sucrose. In order to complete this study, the tests for effectiveness of the molecule formulated with these excipients will be carried out.

HbN Effectiveness Evaluation

The HbN effectiveness test is carried out on a cell model. The measurements carried out concern the percentage viability (percentage of live cells) and the cell density.

The results show that the hemoglobin supplemented with various excipients remains effective on the cells. Indeed, the cells remain more than 95% viable and the cell density is significantly increased compared with the control (×1.7 on average).

A greater effectiveness is observed for the molecule lyophilized in the presence of ascorbic acid and also for the molecule in its lyophilized state without excipient.

Trehalose, for its part, describes a profile similar to that of the non-lyophilized molecule.

Study of the Stability of HbN in the Lyophilized State

For this study, it is necessary to maintain the product lyophilized in the presence or absence of excipients at 37° C. in order to accelerate the degradation of the molecule. It is then reconstituted in water in order to carry out the analyses for monitoring structure, function and concentration.

Monitoring of the Hemoglobin Concentration

The monitoring of the hemoglobin concentration after reconstitution shows the same profile already observed for HbAm. Specifically, no significant difference can be observed up to D2 before beginning a decrease phase synonymous with difficult redispersion.

Monitoring of the Quaternary Structure

In the same way as for HbAm, the profiles of the chromatograms are surprising for ascorbic acid in particular with destructuring of the peak characteristic of hemoglobin.

Monitoring of the Functionality

In the case of HbN, the molecule lyophilized alone without excipient is very strongly oxidized. When the effect of the chosen excipients is studied, trehalose provides protection against oxidation which is stable from D1 to D3. The same is true for ascorbic acid, with a greater protective effect. The profile obtained with a slight increase and then a stability phase is similar to that of HbAm. There is despite everything a significant difference between the two molecules in terms of the initial and final percentage oxidation, twice as high for HbN.

EXAMPLE 2

Samples of 20 ml of HbAm having the following composition were lyophilized:

Sample A (control): HbAm in ultrapure water;
Sample B: HbAm in an aqueous 5 mM ascorbic acid solution;
Sample C: HbAm in an aqueous solution comprising 55 mg/ml of trehalose;
Sample D: HbAm in an aqueous solution comprising 55 mg/ml of trehalose and 5 mM of ascorbic acid.

These lyophilized samples were redispersed in i) ultrapure water, ii) an aqueous 5 mM ascorbic acid solution, iii) a stabilizing solution (=aqueous solution comprising 90 mM of NaCl, 23 mM of Na gluconate, 2.5 mM of $CaCl_2$, 27 mM of Na acetate, 1.5 mM of $MgCl_2$, 5 mM of KCl, pH of 7.1±0.5) or iv) the solution iii) additionally comprising 5 mM of ascorbic acid.

The functionality of the redispersed lyophilizates obtained was measured as indicated in example 1.

The results show that the presence of trehalose during the formulation limits the degradation of HbAm. The percentage of hemoglobin in the redispersed samples C and D (i.e. with trehalose), of around 88%, is significantly higher than that of the samples A and B, of around 82-84%.

In addition, the presence of ascorbic acid during the formulation limits the oxidation associated with the lyophilization.

Lyophilization experiments were carried out with a sample E. This sample E comprises HbAm in an aqueous solution comprising 23 mM of Na gluconate, 2.5 mM of $CaCl_2$, 27 mM of Na acetate, 1.5 mM of $MgCl_2$, 5 mM of KCl, pH of 7.1±0.5, 65 mg/ml of trehalose and 5 mM of ascorbic acid.

It was possible to carry out the lyophilization very satisfactorily.

EXAMPLE 3

Material:
Labconco laboratory lyophilization apparatus
Methods:
1 ml aliquots of HbAm (M101) or HbN (M201)
The 1 ml samples are frozen before lyophilization and dispensed into vials as indicated in table 1 below:

TABLE 1

Summary of the conditions tested. The conditions E and F are positive controls for lyophilization

| Reference | Content | Freezing T |
|---|---|---|
| A | M101 | −20° C. |
| B | M101 | −80° C. |
| C | M201 | −20° C. |
| D | M201 | −80° C. |
| E | 5% Mannitol | −20° C. |
| F | 5% Mannitol | −80° C. |

Once frozen, the vials are placed in the lyophilizer
Results:
Lyophilization Results:

After verification, the −20° C. freezer showed an actual temperature of −17° C.

After loading, the apparatus is pressurized, the samples A and B leave the vial as a foam. The sample C shows limited partial fusion. The other samples, which are in the "ice" zone of the vapor pressure diagram, remain stable. After 30 minutes, the samples D, E and F begin a sublimitation apparently under good conditions but outside control. After operating for 6 hours, the test is stopped. The samples D, E and F appear as an excellent chip, with crystallization clearly apparent. The sample D has a shiny surface suggesting the formation of a skin due to the freezing. The redispersion takes place in a few minutes, but a few "lumps" are present in the sample E.

Results of the HPLC Analyses:

HPLC analyses were carried out in order to verify the purity and the structure of the hemoglobins post-lyophilization and in order to verify whether said hemoglobins were not degraded during the lyophilization.

| Samples | % purity (%) | Clusters (%) | Dissociation (%) |
|---|---|---|---|
| M101 Before Lyoph | 91.80 | 4.01 | 1.49 |
| M101 Post Lyoph | 91.69 | 3.15 | 1.27 |
| M201 Before Lyoph | 86.55 | 5.28 | 2.81 |
| M201 Post Lyoph | 82.32 | 5.60 | 4.39 |

Results of the Hb Assays:

Hemoglobin assays were carried out before and after lyophilization, and once dispersed.

| Samples | Molecules | Before lyophilization (mg/ml) | After lyophilization (mg/ml) |
|---|---|---|---|
| E | M201 | 46.83 | 40.06 |
| F | M101 | 49.05 | 41.87 |

Conclusion:

The first conclusion is that the 2 molecules are lyophilizable, since excellent chips were obtained for the conditions at −80° C. Indeed, the freezing at −20° C. results in the fusion of the molecules during the application of a vacuum.

The sublimation takes place correctly, but, given the duration of the manipulation, there was virtually no secondary desiccation, which, if extended, could only improve in particular the moisture-content and redispersion conditions. The results of the HPLC analyses show that the M201 molecule undergoes a partial degradation (~4%) during the lyophilization. As regards the M101 molecule, it is stable.

The invention claimed is:

1. A container comprising a lyophilizate comprising at least one extracellular hemoglobin selected from the extracellular hemoglobin of *Arenicola marina* and the extracellular hemoglobin of *Nereis*, at least trehalose, 1 to 50 g/L of at least one polyol selected from mannitol and sorbitol, and at least ascorbic acid, wherein the lyophilizate does not comprise any tris-acetate buffer and any cofactor.

2. The container of claim 1, wherein the lyophilizate comprises between 0.1% and 0.5% by weight of water.

3. The container of claim 1, wherein the lyophilizate is a powder which completely redissolves in a hydrophilic liquid, without insoluble residues.

4. The container of claim 1, which comprises glass or plastic.

5. The container of claim 1, which is a glass vial, a bottle, or a flask.

6. The container of claim 1, wherein the lyophilizate comprises a combination of mono- and divalent salts selected from the group consisting of sodium chloride, calcium chloride, magnesium chloride and potassium chloride.

7. The container of claim 1, wherein the lyophilizate is diluted in a diluent.

8. A process for using the container of claim 1, which comprises diluting the lyophilizate with a diluent, in order to provide an initial hemoglobin solution having a pH of between 6.5 and 7.8.

9. A process for storing at least one extracellular hemoglobin, globin protomer or globin of annelids, comprising:
  i) mixing a solution comprising at least one extracellular hemoglobin selected from the extracellular hemoglobin of *Arenicola marina* and the extracellular hemoglobin of *Nereis*, at least trehalose, 1 to 50 g/l of at least one polyol selected from mannitol and sorbitol, and at least ascorbic acid, wherein the solution does not comprise any tris-acetate buffer and any cofactor;
  ii) freezing the mixture at a temperature of between −10° C. and −100° C. for a time of at least 24 h;
  iii) sublimating the frozen mixture for at least 2 h, under vacuum;
  iv) drying the sublimated mixture until a powder is obtained, so as to obtain a lyophilizate; and
  v) storing the lyophilizate in a container.

* * * * *

UNITED STATES PATENT AND TRADEMARK OFFICE
CERTIFICATE OF CORRECTION

| | | |
|---|---|---|
| PATENT NO. | : 12,016,956 B2 | Page 1 of 1 |
| APPLICATION NO. | : 17/014445 | |
| DATED | : June 25, 2024 | |
| INVENTOR(S) | : Zal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 529 days.

Signed and Sealed this
Twenty-second Day of April, 2025

Coke Morgan Stewart
*Acting Director of the United States Patent and Trademark Office*